United States Patent
Wu et al.

(10) Patent No.: US 8,376,936 B2
(45) Date of Patent: Feb. 19, 2013

(54) VIDEOSCOPE PREHEATER

(75) Inventors: Kuei-Huang Wu, Dasi Township, Taoyuan County (TW); Yen-Ming Yeh, Banqiao (TW)

(73) Assignees: Top-Bound Enterprise Co., Ltd., Wugu Township, Taipei County (TW); Morton Surgical Pty. Ltd., Clayton, Vic., (AU)

( * ) Notice: Subject to any disclaimer, the term of this patent is extended or adjusted under 35 U.S.C. 154(b) by 322 days.

(21) Appl. No.: 12/789,857

(22) Filed: May 28, 2010

(65) Prior Publication Data

US 2011/0290773 A1   Dec. 1, 2011

(51) Int. Cl.
*H05B 3/02* (2006.01)
(52) U.S. Cl. ........................ 600/169; 600/133
(58) Field of Classification Search ............ 600/169
See application file for complete search history.

(56) References Cited

U.S. PATENT DOCUMENTS

| | | | | |
|---|---|---|---|---|
| 4,943,705 A * | 7/1990 | Halloran | ........... | 219/385 |
| 6,152,912 A * | 11/2000 | Jansen et al. | ........... | 604/526 |
| 8,172,409 B2 * | 5/2012 | Nagamizu | ........... | 359/512 |
| 2007/0167775 A1 * | 7/2007 | Kochavi et al. | ........... | 600/439 |
| 2010/0016671 A1 * | 1/2010 | Wieters et al. | ........... | 600/169 |

* cited by examiner

*Primary Examiner* — Jerome Jackson, Jr
(74) *Attorney, Agent, or Firm* — Rabin & Berdo, P.C.

(57) ABSTRACT

A videoscope preheater for preheating an endoscope includes: a support tube; an electrical heating layer uniformly coated on an outer surface of the support tube, one side of the electrical heating layer being connected with a power cable for connecting with an external power supply; and a capsule layer coated on an outer surface of the electrical heating layer for fixing and protecting the electrical heating layer and the power cable. The capsule layer is a thermally contractible capsule film, which is fitted around the electrical heating layer and then heated to contract for insulating the electrical heating layer and the support tube from ambient environment. In use, the endoscope is fitted into the support tube and the electrical heating layer is powered on to generate heat and uniformly heat the endoscope. The heating efficiency of the videoscope preheater is controllable by means of adjusting the current and voltage input.

9 Claims, 5 Drawing Sheets

VIDEOSCOPE PREHEATER

BACKGROUND OF THE INVENTION

1. Field of the Invention

The present invention relates generally to a videoscope preheater, and more particularly to an endoscope preheating device, which is easy to be carried and maintained. The heating efficiency of the endoscope preheating device can be easily controlled and the endoscope can be more uniformly preheated with the endoscope preheating device.

2. Description of the Related Art

Following the advance of medical technology, various endoscopes have been developed for examination of internal organs and minimally invasive surgery. In use of an endoscope, it is necessary to extend the endoscope into the human body. Before doing this, the endoscope must be first sterilized and preheated. The endoscope is preheated to avoid fogging due to the heat of human body as well as to reduce uncomfortable feeling of a patient in the therapy.

The conventional endoscope heating devices can be generally divided into vapor heating device, double-boiling device and heat preservation/releasing device. The vapor heating device and the double-boiling device can quickly and stably heat the endoscope. However, such devices are composed of numerous components and have considerably large volume and thus are difficult to be carried. Therefore, the application sites of such devices are limited. Moreover, it is not easy to maintain these devices.

A conventional heat preservation/releasing device includes an envelope containing therein a chemical solution capable of preserving/releasing heat, and a trigger unit for triggering heat releasing reaction. For example, the heat preservation/releasing device can include an envelope containing supersaturated sodium acetate aqueous solution therein and a triggering metal plate positioned in the envelope. The metal plate can be bent to emit microwave radiation for disturbing the original balance state of the sodium acetate aqueous solution. In this case, the sodium acetate will precipitate and crystallize to release heat.

However, with respect to the heat preservation/releasing device, it is hard to control the reaction rate of such chemical reaction. Therefore, it is impossible to control the heating efficiency. Moreover, due to the limitation of the configuration of the envelope, the endoscope can be hardly uniformly heated. That is, those parts adjacent to the envelope will be heated up faster, while those parts distal from the envelope will be heated at lower efficiency. Following the precipitation of the sodium acetate crystal, the envelope will be gradually hardened. Under such circumstance, the endoscope may be stuck in the envelope to cause damage of the fine components on the surface of the endoscope.

It is therefore tried by the applicant to provide an endoscope preheating device, which has simple and lightweight structure and is easy to be carried. Moreover, the heating efficiency of the endoscope preheating device can be easily controlled.

SUMMARY OF THE INVENTION

It is therefore a primary object of the present invention to provide a videoscope preheater, which has a simple structure and is easy to be carried and maintained. The heating efficiency of the videoscope preheater can be easily controlled to uniformly preheat an endoscope.

To achieve the above and other objects, the videoscope preheater of the present invention is an endoscope preheating device including a support tube with a predetermined length, an electrical heating layer coated on an outer surface of the support tube, and a capsule layer coated on an outer surface of the electrical heating layer. The endoscope can be fitted into the support tube and heated by the electrical heating layer. A rear end of the electrical heating layer is provided with a power cable for connecting with an external power supply. The capsule layer is a thermally contractible capsule film. The thermally contractible capsule film is fitted around the electrical heating layer and then heated to contract. Accordingly, the thermally contractible capsule film can tightly attach to the outer surfaces of the electrical heating layer and the support tube to insulate the electrical heating layer and the support tube from the ambient environment.

In the above videoscope preheater, the electrical heating layer includes a conductive rubber layer. Metal leads are planted in two ends of a surface of the conductive rubber layer. Two insulation layers are respectively overlaid on upper and lower surfaces of the conductive rubber layer. The support tube is made of polymer material.

In the above videoscope preheater, a rear end of the power cable is provided with a plug. The power cable has a positive electrode wire and a negative electrode wire in parallel to the positive electrode wire. The positive and negative electrode wires are respectively connected to two electrodes of the electrical heating layer. An overhand knot is tied at a branch-off point of the positive and negative electrode wires to prevent the positive and negative electrode wires from further splitting off from each other along the fissure. The external power supply is selected from the group consisting of a car power socket, a transformer and a battery pack.

In the above videoscope preheater, a rear end of the thermally contractible capsule film protrudes from a rear end of the support tube, whereby after heated, the rear end of the thermally contractible capsule film contracts to form a contracted hub section. A polymer film is further disposed between the electrical heating layer and the capsule layer. The polymer film serves to reduce the frictional resistance between the electrical heating layer and the capsule layer so as to increase the assembling efficiency.

In the above videoscope preheater, the external power supply is provided with a controller for regulating voltage and current. The heating power of the videoscope preheater can be easily adjusted by means of adjusting the magnitude of the input voltage and the magnitude of the input current. In this case, the endoscope can be more quickly and more uniformly preheated with the videoscope preheater.

The present invention can be best understood through the following description and accompanying drawings, wherein:

DETAILED DESCRIPTION OF THE PREFERRED EMBODIMENTS

Figure 1:
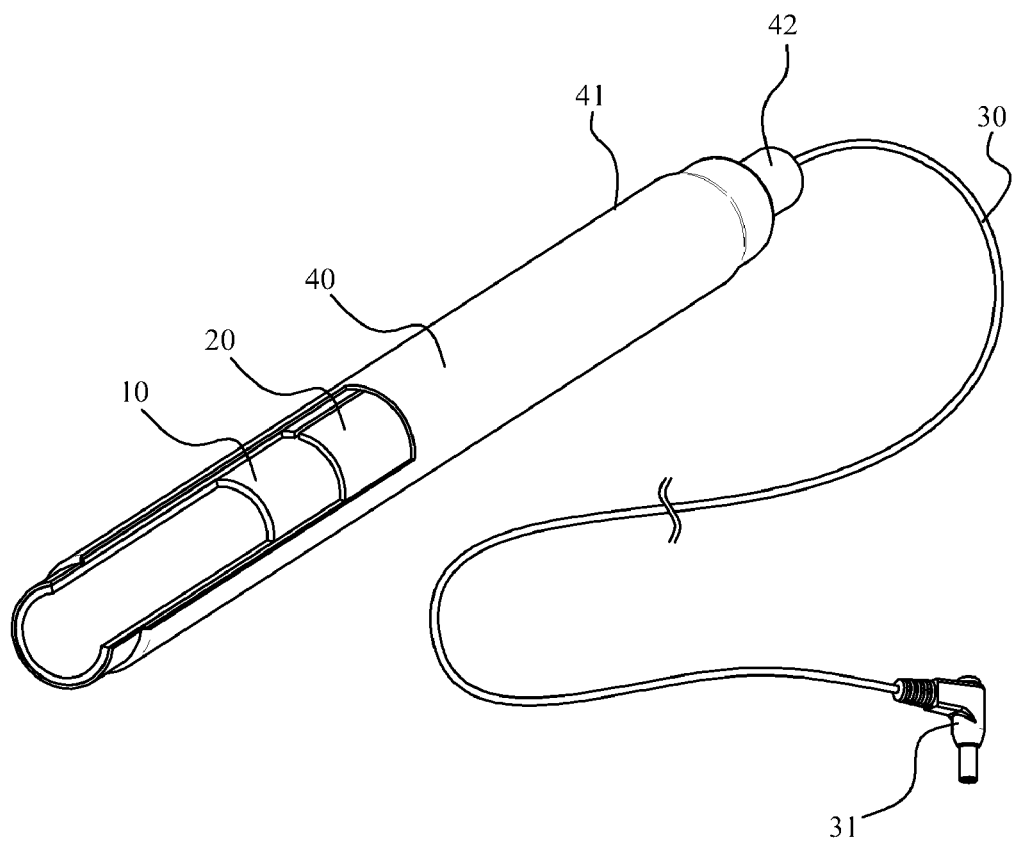
FIG. 1 is a perspective sectional view of a first embodiment of the present invention.
Figure 3:
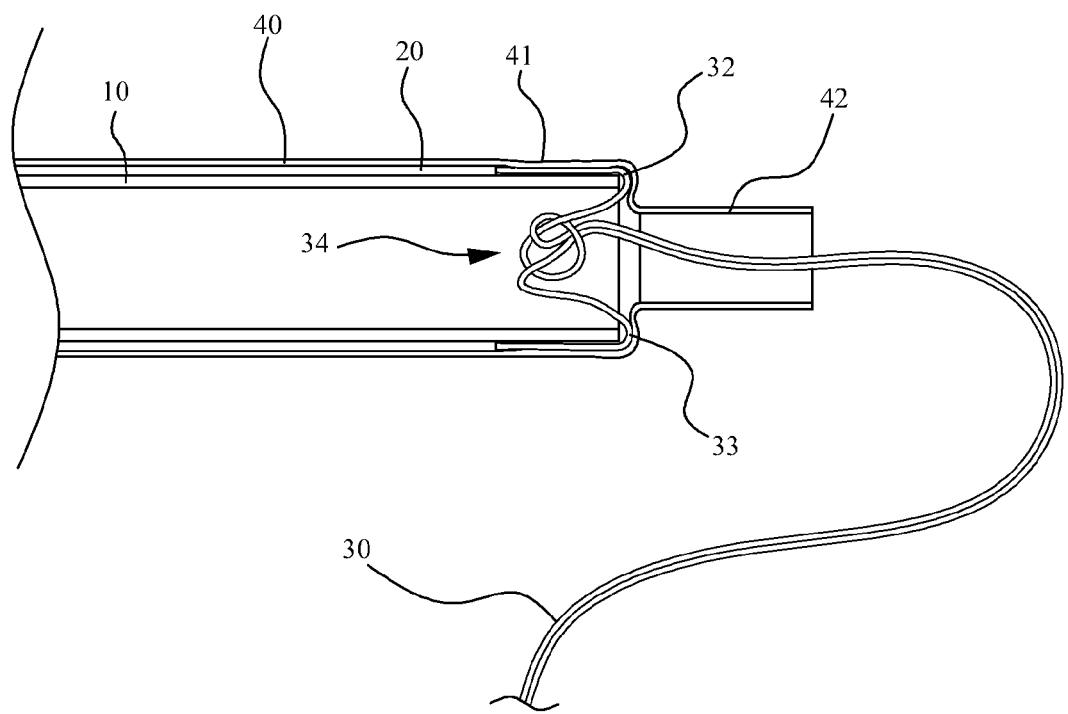
FIG. 3 is a sectional view according to FIG. 1.
Figure 5:
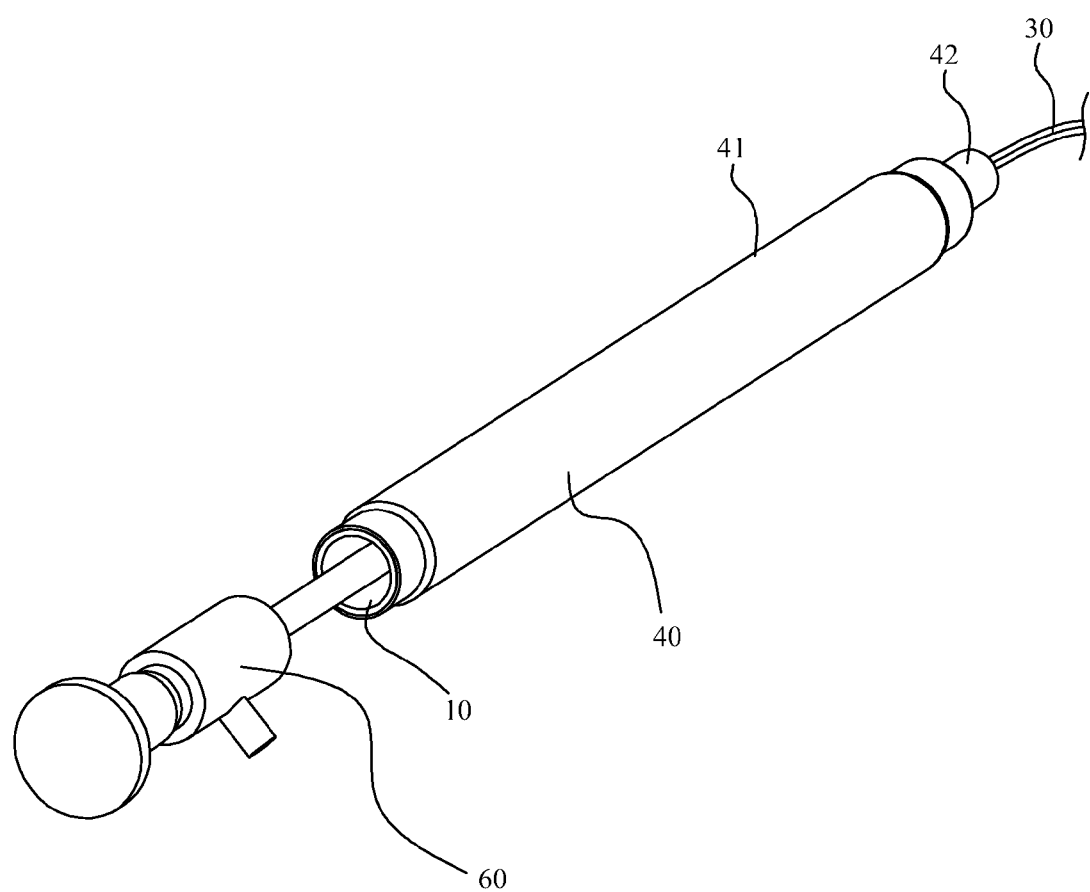
FIG. 5 is a perspective view showing the use of the present invention.

Please refer to FIGS. 1, 3 and 5. According to a first embodiment, the present invention includes a support tube 10. The support tube 10 has an inner diameter slightly larger than an outer diameter of an endoscope 60, whereby the endoscope 60 can be easily fitted into the support tube 10. An outer surface of the support tube 10 is uniformly annularly coated with an electrical heating layer 20. The electrical heating layer 20 has a length shorter than that of the support tube 10 to enclose a middle section of the support tube 10. One side of the electrical heating layer 20 is connected with a power cable 30. A rear end of the power cable 30 has a plug 31 for connecting with an external power supply. An outer surface of the electrical heating layer 20 is coated with a capsule layer 40. In this embodiment, the capsule layer 40 is a thermally contractible capsule film 41. The thermally contractible capsule film 41 is fitted around the electrical heating layer 20 and then heated to contract. In this case, the thermally contractible capsule film 41 can smoothly and tightly attach to the outer surfaces of the electrical heating layer 20 and the support tube 10. The thermally contractible capsule film 41 and the support tube 10 cooperate with each other to fully enclose the electrical heating layer 20 which is shorter than the support tube 10 and the thermally contractible capsule film 41. Accordingly, the front and rear ends of the electrical heating layer 20 are prevented from contacting with the ambient environment.

In this embodiment, the support tube 10 is made of polymer material. As necessary, the external power supply is selected from the group consisting of a car power socket, a transformer and a battery pack.

In the preferred embodiment of FIG. 1, the capsule layer 40 has a length longer than that of the support tube 10. A front end of the thermally contractible capsule film 41 is free from the power cable 30. The power cable 30 extends out of a rear end of the thermally contractible capsule film 41. The front end of the thermally contractible capsule film 41 is flush with a front end of the support tube 10. The rear end of the thermally contractible capsule film 41 protrudes from a rear end of the support tube 10. After heated, the rear end of the thermally contractible capsule film 41 contracts to form a contracted hub section 42. The contracted hub section 42 not only enhances the insulation property of the entire device, but also supports the power cable 30 to avoid over-flexure or breakage of the power cable 30 due to over-flexure.

Figure 2:
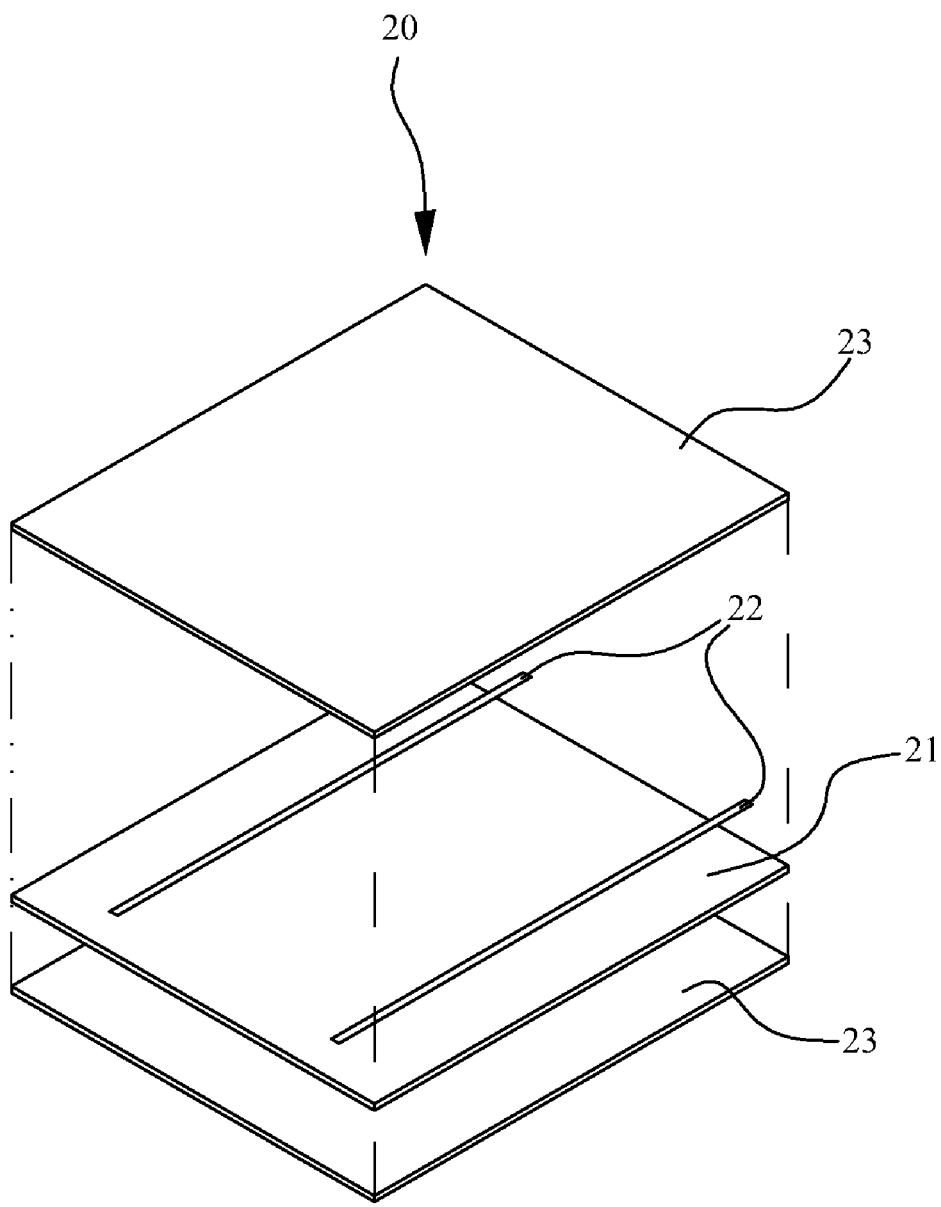
FIG. 2 is a perspective exploded view of the electrical heating layer of the first embodiment of the present invention.

Please refer to FIG. 2. The electrical heating layer 20 is preferably a heating structure made of special electrical heating material. The electrical heating layer 20 includes a conductive rubber layer 21. Metal leads 22 are planted in two ends of the surface of the conductive rubber layer 21 by means of thermal pressing, sewing or insertion. Two insulation layers 23 are respectively overlaid on and attached to upper and lower surfaces of the conductive rubber layer 21 to form the electrical heating layer 20. The metal leads 22 are connected with the positive and negative electrode wires in parallel or in series. After the power is turned on, the conductive rubber layer 21 will generate heat.

Further referring to FIG. 3, in the preferred embodiment, the power cable 30 has a positive electrode wire 32 and a negative electrode wire 33 in parallel to the positive electrode wire 32. The positive and negative electrode wires 32, 33 are respectively connected to the two electrodes of the electrical heating layer 20. An overhand knot 34 is tied at the branch-off point of the positive and negative electrode wires 32, 33 to prevent the positive and negative electrode wires 32, 33 from further splitting off from each other along the fissure.

Figure 4:
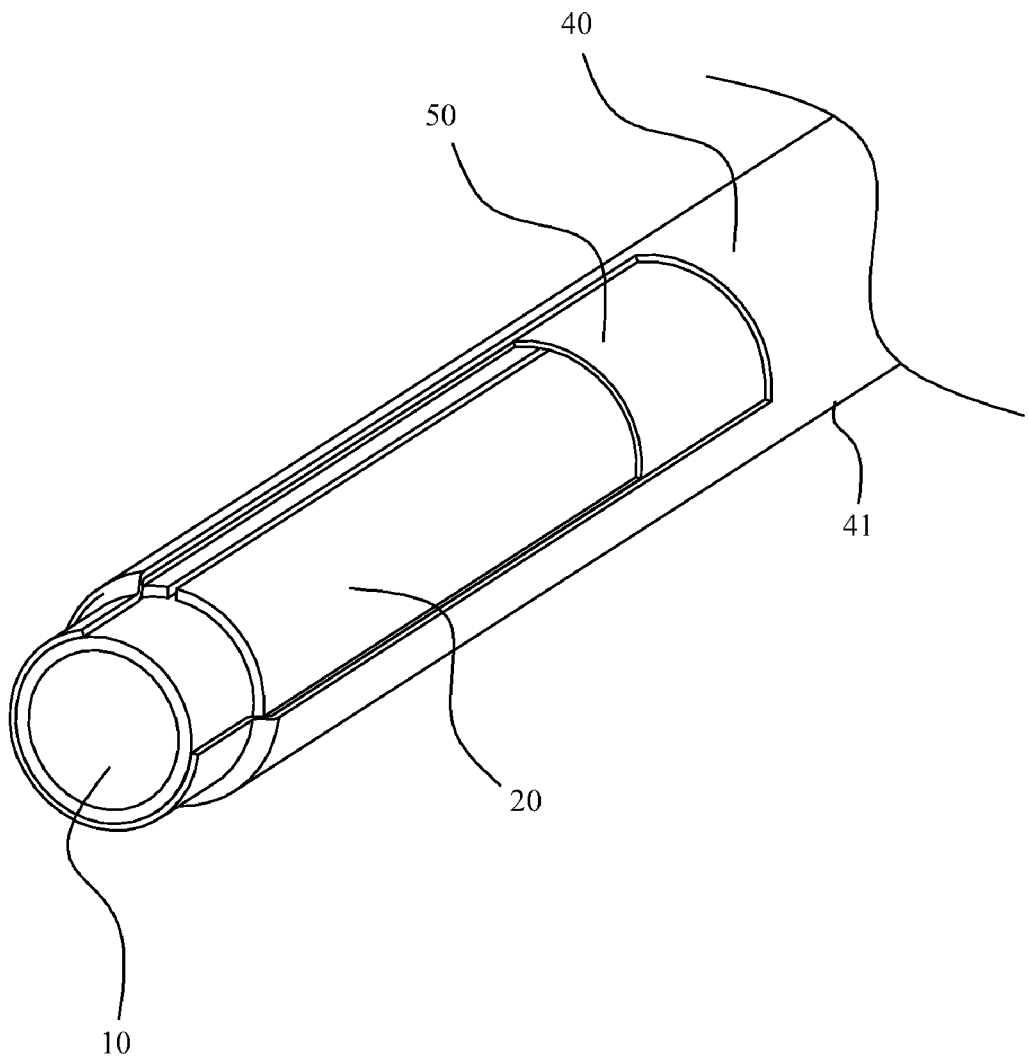
FIG. 4 is a perspective sectional view of a second embodiment of the present invention.

Please refer to FIG. 4, which shows a second embodiment of the present invention. In the second embodiment, a polymer film 50 is further disposed around the outer surface of the electrical heating layer 20. The polymer film 50 has a surface frictional coefficient lower than that of the electrical heating layer 20. The outer surface of the polymer film 50 is coated with a capsule layer 40. The polymer film 50 serves to reduce the frictional resistance against the capsule layer 40 in the assembling operation. Accordingly, the assembling operation can be completed at higher efficiency.

Please refer to FIG. 5, which shows the use of the videoscope preheater of the present invention. First, the endoscope 60 is fitted into the support tube 10. Then, a suitable external power supply is selectively used to supply power according to the site of use. After connected to the external power supply, the electrical heating layer 20 is powered on to generate heat. The heat generated by the electrical heating layer 20 is variable with the current and voltage. Therefore, a user can easily regulate the heat generation efficiency of the present invention by means of adjusting magnitude of the current and magnitude of the voltage.

In conclusion, in the present invention, the electrical heating layer is annularly disposed around the support tube for heating the endoscope. The endoscope preheating device of the present invention has simple and lightweight structure and is easy to carry. Moreover, it is easy to maintain the endoscope preheating device. In addition, the present invention is electrically powered to heat the endoscope. Accordingly, the heating power of the endoscope preheating device can be easily adjusted by means of adjusting the magnitude of the input current and magnitude of the input voltage. In this case, the endoscope can be more quickly and more uniformly preheated with the present invention.

The above embodiments are only used to illustrate the present invention, not intended to limit the scope thereof. Many modifications of the above embodiments can be made without departing from the spirit of the present invention.

What is claimed is:

1. A videoscope preheater for removably receiving an endoscope and preheating the endoscope, the videoscope preheater comprising:
    a support tube for covering the endoscope and with a predetermined length, wherein the endoscope can be removably fitted into the support tube;
    an electrical heating layer coated on an outer surface of the support tube;
    a power cable attached to a rear end of the electrical heating layer, the power cable for connecting with an external power supply; and
    a capsule layer coated on an outer surface of the electrical heating layer, wherein the endoscope can be heated by the electrical heating layer, the capsule layer being a thermally contractible capsule film, the thermally contractible capsule film being fitted around the electrical heating layer and then heated to contract so that the thermally contractible capsule film tightly attaches to the outer surfaces of the electrical heating layer and the support tube to insulate the electrical heating layer and the support tube from ambient environment.

2. The videoscope preheater as claimed in claim 1, wherein the external power supply is selected from the group consisting of a car power socket, a transformer and a battery pack.

3. The videoscope preheater as claimed in claim 1, wherein the support tube is made of polymer material.

4. The videoscope preheater as claimed in claim 1, wherein the electrical heating layer comprises:
    a conductive rubber layer;
    metal leads disposed in two ends of a surface of the conductive rubber layer, and
    two insulation layers being respectively overlaid on upper and lower surfaces of the conductive rubber layer.

5. The videoscope preheater as claimed in claim 1 further comprising a plug provided at a rear end of the power cable, and
wherein the electric heating layer includes two electrodes, further wherein the power cable has a positive electrode wire and a negative electrode wire in parallel with the positive electrode wire, the positive and negative electrode wires being respectively connected to the two electrodes of the electrical heating layer, an overhand knot being tied at a branch-off point of the positive and negative electrode wires.

6. The videoscope preheater as claimed in claim 1, wherein a rear end of the thermally contractible capsule film protrudes from a rear end of the support tube, wherein after the thermally contractible film is heated, the rear end of the thermally contractible capsule film contracts to form a contracted hub section.

7. The videoscope preheater as claimed in claim 1, further comprising a polymer film disposed between the electrical heating layer and the capsule layer.

8. The videoscope preheater as claimed in claim 1, wherein the external power supply is provided with a controller for regulating voltage and current.

9. A videoscope preheater for removably receiving an endoscope and preheating the endoscope, the videoscope preheater comprising:
 a support tube for covering the endoscope and with a predetermined length, wherein the endoscope can be removably fitted into the support tube;
 an electrical heating layer coated on an outer surface of the support tube, the electrical heating layer including
  a conductive rubber layer,
  metal leads disposed at two ends of a surface of the conductive rubber layer, and
  two insulation layers being respectively overlaid on upper and lower surfaces of the conductive rubber layer;
 a power cable attached to a rear end of the electrical heating layer, the power cable for connecting with an external power supply; and
 a capsule layer coated on an outer surface of the electrical heating layer, wherein the endoscope can be heated by the electrical heating layer, the capsule layer being a thermally contractible capsule film, the thermally contractible capsule film being fitted around the electrical heating layer,
wherein, the thermally contractible capsule film tightly attaches to outer surfaces of the electrical heating layer and the support tube to insulate the electrical heating layer and the support tube from ambient environment, and a rear end of the thermally contractible capsule film protrudes from a rear end of the support tube, the rear end of the thermally contractible capsule film contracts to form a contracted hub section.

* * * * *